US006784165B1

(12) United States Patent
Martin (10) Patent No.: US 6,784,165 B1
(45) Date of Patent: Aug. 31, 2004

(54) TREATMENT OF HEART RHYTHM DISTURBANCES WITH $N^6$-SUBSTITUTED-5'-(N-SUBSTITUTED) CARBOXAMIDOADENOSINES

(75) Inventor: Pauline L. Martin, Boston, MA (US)

(73) Assignee: Aderis Pharmaceuticals, Inc., Richmond, VA (US)

( * ) Notice: Subject to any disclaimer, the term of this patent is extended or adjusted under 35 U.S.C. 154(b) by 77 days.

(21) Appl. No.: 09/713,307

(22) Filed: Nov. 16, 2000

Related U.S. Application Data (60) Provisional application No. 60/167,014, filed on Nov. 23, 1999.

(51) Int. Cl.[7] .................. A61K 31/70; C07H 19/167
(52) U.S. Cl. .......................... 514/46; 536/27.22
(58) Field of Search ................... 514/46; 536/27.22

(56) References Cited

U.S. PATENT DOCUMENTS

| | | |
|---|---|---|
| 3,502,649 A | 3/1970 | Thiel et al. |
| 3,509,129 A | 4/1970 | Kampe et al. |
| 3,590,029 A | 6/1971 | Koch et al. |
| 3,781,273 A | 12/1973 | Kampe et al. |
| 3,851,056 A | 11/1974 | Stork et al. |
| 3,901,876 A | 8/1975 | Vorbrüggen et al. |
| 3,931,401 A | 1/1976 | Prasad et al. |
| 3,966,916 A | 6/1976 | Kampe et al. |
| 4,029,884 A | 6/1977 | Stein et al. |
| 4,090,021 A | 5/1978 | Vorbrüggen |
| 4,167,565 A | 9/1979 | Stein et al. |
| 4,224,438 A | 9/1980 | Fauland et al. |
| 4,514,405 A | 4/1985 | Irmscher et al. ............ 514/46 |
| 4,673,563 A | 6/1987 | Berne et al. .................. 424/9 |
| 4,727,064 A | 2/1988 | Pitha ......................... 514/58 |
| 4,738,954 A | 4/1988 | Hamilton et al. ............ 514/46 |
| 4,764,604 A | 8/1988 | Müller ...................... 536/103 |
| 4,868,160 A | 9/1989 | Hamilton et al. ............ 514/46 |
| 5,024,998 A | 6/1991 | Bodor ....................... 514/58 |
| 5,032,583 A | 7/1991 | Evans ........................ 514/46 |
| 5,219,839 A | 6/1993 | Bru-Magniez et al. ....... 514/46 |
| 5,219,840 A * | 6/1993 | Gadient et al. .............. 514/46 |
| 5,310,731 A | 5/1994 | Olsson et al. ............... 514/46 |
| 5,364,862 A | 11/1994 | Spada et al. ................. 514/303 |
| 5,424,297 A | 6/1995 | Rubio et al. ................. 514/46 |
| 5,789,416 A | 8/1998 | Lum et al. |
| 6,048,865 A | 4/2000 | Baraldi |
| RE37,045 E | 2/2001 | Olsson et al. ................ 514/46 |
| 6,211,165 B1 * | 4/2001 | Liang et al. ................. 514/46 |
| 6,307,054 B1 * | 10/2001 | Truesdale et al. ........... 546/296 |
| 6,329,349 B1 * | 12/2001 | Liang et al. ................. 514/46 |

FOREIGN PATENT DOCUMENTS

| | | |
|---|---|---|
| DE | 2 007 273 | 8/1971 |
| EP | 0 169 009 A2 | 1/1986 |
| JP | 58-167599 | 10/1983 |
| WO | WO 99/24450 A2 | 5/1999 |
| WO | WO 99/24450 A3 | 8/1999 |
| ZA | 67/7630 | 4/1968 |

OTHER PUBLICATIONS

Belardinelli, L. et al., "The Cardiac Effects of a Novel $A_1$–Adenosine Receptor Agonist in Guinea Pig Isolated Heart," *J. Pharmacol. & Experimental Therapeut.* 271:1371–1382, The American Society for Pharmacology and Experimental Therapeutics (1994) (Issue No. 3; Dec., 1994).

Daly, J.W., "Adenosine Receptors: Targets for Future Drugs," *J. Med. Chem.* 25:197–207, American Chemical Society (1982) (Issue No. 3; Mar., 1982).

Daly, J.W. et al., "Structure–Activity Relationships for $N^6$–Substituted Adenosines at a Brain $A_1$–Adenosine Receptor with a Comparison to an $A_2$–Adenosine Receptor Regulating Coronary Blood Flow," *Biochem. Pharmacol.* 35:2467–2481, Pergamon Journals Ltd. (1986) (Issue No. 15; Aug. 1, 1986).

Fleysher, M.H. et al., "Synthesis and biological activity of some new $N^6$–substituted purine nucleosides," *Chem. Abstracts* 72:349, Abstract No. 3706g, American Chemical Society (1970) (Jan. 5, 1970).

(List continued on next page.)

*Primary Examiner*—James O. Wilson
*Assistant Examiner*—L E Crane
(74) *Attorney, Agent, or Firm*—Sterne, Kessler, Goldstein & Fox P.L.L.C.

(57) ABSTRACT

The present invention discloses a method for treating heart rhythm disturbances in a mammal in need thereof by the administration of $N^6$-substituted-5'(N-substituted) carboxamidoadenosines. More particularly, the invention is directed to a method for treatment of heart rhythm disturbances in a mammal that would benefit from the induction of negative dromotropic and/or negative chronotropic actions, comprising the administration to said mammal an effective amount of a compound of the Formula:

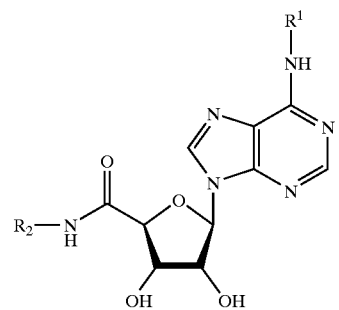

or a pharmaceutically acceptable salt or ester thereof; wherein $R_1$ is $C_{3-7}$ secondary alkyl, or $C_{3-8}$ cycloalkyl; and $R_2$ is $C_{1-4}$ alkyl or $C_{3-5}$ cycloalkyl The invention is also directed to novel dosage forms comprising said compounds.

30 Claims, 2 Drawing Sheets

OTHER PUBLICATIONS

Fox, I.H. and L. Kurpis, "Binding Characteristics of an Adenosine Receptor in Human Placenta," *J. Biol. Chem.* 258:6952–6955, American Society of Biological Chemists, Inc. (1983) (Issue No. 11; Jun. 10, 1983).

Goodman, L., "Chemical Syntheses and Transformations of Nucleosides," in: *Basic Principles in Nucleic Acid Chemistry*, Ts'o, P.O.P., ed., Academic Press, New York, publ., pp. 150–151 (1974).

Kenakin, T.P. and N.B. Pike, "An in vitro analysis of purine–mediated renal vasoconstriction in rat isolated kidney," *Br. J. Pharmac.* 90:373–381, The Macmillan Press Ltd. (1987) (Issue No. 2; Feb., 1987).

Olsson, R.A. et al., "Use of Structure–Activity Relationships in the Study of Adenosine Receptors," in: *Methods in Pharmacology*, Paton, D,M., ed., Plenum Press, NY, pp. 293–304 (1985) vol. No. 6.

Olsson, R.A. et al., "$N^6$–Substituted N–Alkyladenosine–5'–uronamides: Bifunctional Ligands Having Recognition Groups for A1 and A2 Adenosine Receptors," *J. Med. Chem.* 29:1683–1689, American Chemical Society (1986) (Issue No. 9; Sep., 1986).

Panzacchi, G. et al., "Effects of adenosine receptor agonists on renal function in anaesthetized rats," *J. Hypertension* 15:1785–1789, Rapid Science Publishers (1997) (Issue No. 12, Part II, Dec., 1997).

Paton, D.M. et al., "Potency of $N^6$–modified N–alkyl adenosine–5'–uronamides at presynaptic adenosine receptors in guinea–pig ileum," *Naunyn–Schmiedeberg's Arch. Pharmacol.* 335:301–304, Springer–Verlag (1987) (Issue No. 3; Mar., 1987).

Schmidt, R.R. and H.–J. Fritz, "Synthesis and Structure of Inosine–5'–carboxylic Acid and Derivatives," *Chem. Ber.* 103:1867–1871, Weinheim/Bergsr. VCH Verlagsgesellschaft mbH. (1970).

Schwabe, U., "General Aspects of Binding of Ligands to Adenosine Receptors," in: *Regulatory Function of Adenosine*, Berne, R.M. et al., eds., Martinus Nijhoff, Boston, publ., pp. 77–96 (1983).

Snowdy, S. et al., "A comparison of an $A_1$ adenosine receptor agonist (CVT–510) with diltiazem for slowing of AV nodal conduction in guinea–pig," *Brit. J. Pharmacol.* 126:137–146, Stockton Press (Jan. 1999).

Stein, H.H., "Ethyl–Adenosine–5'–carboxylate. A Potent Vasoactive Agent in the Dog," *J. Med. Chem.* 16:1306–1308, American Chemical Society (1973) (Issue No. 11, Nov., 1973).

Stein, H.H. and P. Somani, "Cardiovascular Effects of Nucleoside Analogs," *Annals N.Y. Acad. Sci.* 255:380–389, The New York Academy of Sciences (1975).

English Language Abstract of DE 2 007 273, Derwent World Patents Index (Dialog File 351), WPI Accession No. 71–56157s. (Feb. 18, 1970).

Kollias–Baker, C., et al., "Allosteric Enhancer PD 81,723 Acts by Novel Mechanism to Potentiate Cardiac Actions of Adenosine," *Circulation Res.* 75:961–971, American Heart Association, Inc. (1994), (Issue No. 6; Dec., 1994).

Belardinelli et al., U.S. patent application Publication No. US 2001/0008883 A1, Publication Date: Jul. 19, 2001.

Cox, B. F. et al., "Cardiovascular and Metabolic Effects of Adenosine A–Receptor Agonists in Streptozotocin–Treated Rats," *J. Cardio Pharmacol.* 29:417–426, Lippincott–Raven Publishers (1987), (Mar., 1997).

Merkel, L.A. et al., "In Vitro and in Vivo Characterization of an A1–Selective Adenosine Agonist, RG14202," *J. Pharmacol. Exp. Ther.* 265:699–706, Williams & Wilkins (1993), (Issue No. 2).

Lorenzen, A., et al., "Activation of Various Subtypes of G–Protein α Subunits by Partial Agonists of the Adenosine $A_1$ Receptor," *Biochem. Pharmacol.* 56: 1287–1293, Elsevier Science, Inc. (Nov. 1998).

Roelen, H., et al., "$N^6$, C8–Disubstituted Adenosine Derivatives as Partial Agonists for Adenosine $A_1$ Receptors," *J. Med. Chem.* 39:1463–1471, American Chemical Society (1996) (Abstract published Feb. 15, 1996).

van der Wenden, E.M., et al., "5'–Substituted Adenosine Analogs as New High–Affinity Partial Agonists for the Adenosine $A_l$ Receptor," *J. Med. Chem.* 41:102–108, American Chemical Society (Jan. 1998).

\* cited by examiner

TREATMENT OF HEART RHYTHM DISTURBANCES WITH N⁶-SUBSTITUTED-5'-(N-SUBSTITUTED) CARBOXAMIDOADENOSINES

This application claims the priority benefit under 35 U.S.C. §119(e) of the earlier filing date of U.S. Provisional Appl. No. 60/167,014, filed on Nov. 23, 1999, the entirety of which is incorporated by reference herein.

BACKGROUND OF THE INVENTION

1. Field of the Invention

The present invention relates to the use of particular adenosine $A_1$ agonists belonging to a class of N⁶-substituted-5'-(N-substituted) carboxamidoadenosines in the treatment of heart rhythm disturbances in mammals, and to novel dosage forms for practicing this new use.

2. Related Art

In the mammalian heart, in order to circulate blood, contraction of the ventricles is initiated by an electrical impulse in the sinoatrial (SA) node that then passes through the atrioventricular (AV) node to the ventricles. Consistent rhythmic impulses produce a regular heart beat when the heart is functioning normally.

Various dysfunctions can occur in the heart to disturb the regular heart beat pattern and produce arrhythmias. For example, a condition of excessively rapid heart beats can occur that is defined as tachycardia. Tachycardia can originate from excessively rapid discharges from a malfunctioning SA node, electrical impulses passing through accessory pathways that prompt beats before they would normally occur, or re-entry of impulses in the AV node. In such cases, the disorder has been referred to as paroxsymal supraventricular tachycardia (PSVT), which in some patients can progress to congestive heart failure. Another heart rhythm disturbance, referred to as atrial fibrillation/flutter (AF), is characterized by a rapid and disordered beating of the atria, and is associated with an increased incidence of stroke. The above described heart rhythm disturbances can be classified as supraventricular tachyarrhythmias. Symptoms of these disorders can include discomfort due to palpitations, fatigue, dyspnea, as well as a sensation of lightheadedness and/or dizziness.

Adenosine is well-known to slow heart rate (negative chronotropic effect) and slow impulse conduction through the AV node (negative dromotropic effect) (Berne et al., U.S. Pat. No. 4,673,563; Belardinelli et al., *Journal of Pharmacology and Experimental Therapeutics* 271: 1371(1994)). Adenosine is currently used in the treatment of PSVT, but it has not proven efficacious in converting AF to normal sinus rhythm.

Adenosine acts through multiple receptor subtypes, termed $A_1$, $A_{2A}$, $A_{2B}$, and $A_3$. The adenosine $A_1$ receptor mediates adenosine's negative chronotropic and negative dromotropic effects as well as directly depressing atrial (but not ventricular) contractility. The adenosine $A_{2A}$ receptor mediates adenosine's action of dilating coronary arteries. The localization and function of adenosine $A_{2B}$ and $A_3$ receptors in the heart have not been well defined.

Since PSVT can result from abnormally frequent impulses affecting the AV node and since the adenosine $A_1$ receptor mediates adenosine's negative dromotropic effect, one strategy to terminate PSVT is to use a selective adenosine $A_1$ receptor agonist to slow impulse conduction through the AV node (Belardinelli et al., *Journal of Pharmacology and Experimental Therapeutics* 271: 1371 (1994); Snowdy et al., *British Journal of Pharmacology* 126: 137 (999)).

However, adenosine $A_1$ receptor agonists that have been heretofore studied for this purpose lacked the necessary potency, selectivity, oral bioavailability and/or pharmacodynamic activity. In addition, prior art adenosine $A_1$ agonists have also been shown to be hypotensive, a side effect that would worsen symptoms of patients experiencing heart rhythm disturbances.

A series of N⁶-substituted-5'-(N-substituted) carboxamidoadenosine derivatives have been previously described. These compounds are selective adenosine $A_1$ receptor agonists (Olsson, R. and Thompson, R., U.S. Pat. No. 5,310,731), having utility as vasodilatory or antihypertensive agents.

SUMMARY OF THE INVENTION

The present invention is directed to a method for treatment of heart rhythm disturbances in a mammal that would benefit from the induction of negative dromotropic action, negative chronotropic action, or a combination thereof, comprising:

administering to a mammal in need of such treatment an effective amount of a compound of Formula I:

or a pharmaceutically acceptable salt or ester thereof, wherein $R_1$ is $C_{3-7}$ secondary alkyl, $C_{3-8}$ cycloalkyl, or $C_7$ bicycloalkyl; and $R_2$ is $C_{1-4}$ alkyl, $C_{1-4}$ hydroxyalkyl or $C_{3-5}$ cycloalkyl.

Such heart rhythm disturbances include supraventricular tachyarrhythmias, such as paroxysmal supraventricular tachycardia (PSVT) and atrial fibrillation/flutter (AF).

The present invention is also directed to novel intravenous and oral dosage forms comprising particular concentrations of one or more compounds of Formula I.

The present invention is also directed to the use of a compound of Formula I in the manufacture of a medicament for treating heart rhythm disturbances in a mammal that would benefit from the induction of negative dromotropic action, negative chronotropic action, or a combination thereof.

DETAILED DESCRIPTION OF THE PREFERRED EMBODIMENTS

It has now been discovered that specific $N^6$-substituted-5'-(N-substituted)carboxamidoadenosines, defined by Formula I above, possess particularly desirable pharmacological properties useful in the treatment of heart rhythm disturbances. These compounds possess one or more of unexpected potency, selectivity, oral bioavailability, and pharmacodynamic activity.

Thus, the present invention is directed to a method for treatment of heart rhythm disturbances in a mammal that would benefit from the induction of negative dromotropic action, negative chronotropic action, or a combination thereof, comprising:

administering to a mammal in need of such treatment an effective amount of a compound of Formula I:

or a pharmaceutically acceptable salt or ester thereof, wherein $R_1$ is $C_{3-7}$ secondary alkyl, or $C_{3-8}$ cycloalkyl; and
$R_2$ is $C_{1-4}$ alkyl, $C_{1-4}$ hydroxyalkyl or $C_{3-5}$ cycloalkyl.

Useful values of $R_1$ include isopropyl, 2-butyl, 2-pentyl, 3-pentyl, 2-hexyl, 3-hexyl, 2-heptyl, 3-heptyl, 4-heptyl, cyclopropyl, cyclopentyl, cyclohenyl, cycloheptyl and norbornyl. Preferred values of $R_1$ include 3-pentyl, cyclopentyl or norbornyl, more preferably 3-pentyl or cyclopentyl. Useful values of $R_2$ include methyl ethyl, propyl, isopropyl, butyl, isobutyl, sec-butyl, t-butyl, hydroxymethyl, hydroxyethyl, hydroxypropyl, cyclopropyl, cyclobutyl, and cyclopentyl. Preferred values of $R_2$ include methyl, ethyl, hydroxyethyl, isopropyl or cyclopropyl, more preferably ethyl or cyclopropyl.

Useful compounds include:
$N^6$-cyclopentyl-5'-(N-ethyl)carboxamidoadenosine,
$N^6$-cyclopentyl-5'-(N-cyclopropyl)carboxamidoadenosine,
$N^6$-(3-pentyl)-5'-(N-ethyl)carboxamidoadenosine,
$N^6$-cyclopentyl-5'-(N-methyl)carboxamidoadenosine, or
$N^6$-cyclopentyl-5'-(N-t-butyl)carboxamidoadenosine,
as well as pharmaceutically acceptable salts and esters thereof.

This invention utilizes the administration of $N^6$-substituted-5'-(N-substituted)carboxamidoadenosines of Formula I for treating heart rhythm disturbances in mammals. The treatment of a heart rhythm disturbance episode and optional prophylactic maintenance therapy to minimize the further occurrence of heart rhythm disturbances are both contemplated as useful aspects of the present invention. Such heart rhythm disturbances include supraventricular tachyarrhythmias, such as paroxysmal supraventricular tachycardia (PSVT) and a trial fibrillation/flutter (AF).

In a preferred aspect of the invention, an $N^6$-substituted-5'-(N-substituted)carboxamidoadenosine is administered by intravenous infusion of about 0.001 µg/kg to about 100 µg/kg, preferably about 0.005 µg/kg to about 1 µg/kg, more preferably about 0.01 µg/kg to about 0.5 µg/kg, to treat a heart rhythm disturbance. The duration of this infusion can be tailored to the individual patient. Useful infusion periods are from about 2 to about 60 minutes, preferably about 10 to about 30 minutes. Afterwards, an $N^6$-substituted-5'-(N-substituted) carboxamidoadenosine can be optionally, orally administered in a suitable pharmaceutical composition at a dose within the range of about 0.001 µg/kg to about 100 µg/kg, preferably about 0.01 µg/kg to about 10 µg/kg, more preferably about 0.1 µg/kg to about 8 µg/kg This dose is preferably adjusted to optimize the individual patient's response. The oral administration is particularly useful as prophylactic maintenance therapy to minimize the episodic occurrence of these heart rhythm disturbances.

The most preferred dose administered intravenously is about 0.1 to about 10 µg/kg/min, while the most preferred dose administered orally is about 1 to about 50 µg/kg as needed, up to four times a day.

The most preferred compounds for this utility are:
$N^6$-cyclopentyl-5'-(N-ethyl)carboxamidoadenosine, and
$N^6$-cyclopentyl-5'-(N-cyclopropyl)carboxamidoadenosine.

$N^6$-cyclopentyl-5'-(N-ethyl)carboxamidoadenosine (a compound of Formula I wherein $R_1$ is cyclopentyl and $R_2$ is ethyl) is also known as 1-[6-(cyclopentylamino)-9H-purin-9-yl]-1-deoxy-N-ethyl-β-D-ribofuranuronamide or $N^6$-cyclopentyladenosine-5'-ethylcarboxamide.

Further, it has been discovered that a separation exists between (a) the ability of compounds of Formula I to slow impulse conduction in the heart as evidenced by their negative dromotropic activity and negative chronotropic activity as compared with (b) hypotensive activity or the lack thereof for such compounds. Thus, these compounds can be dosed in a manner to treat heart rhythm disturbances by decreasing heart rate while not affecting blood pressure. This is a highly desirable property which is not suggested by the prior art. Based upon the prior art, these compounds would be expected to have hypotensive activity. It would be expected that administration of an adenosine $A_1$ agonist would worsen symptoms of patients experiencing heart rhythm disturbances and complicate therapeutic intervention.

It has also been discovered that the negative dromotropic effect of compounds of Formula I are dependent upon heart rate. As heart rate is increased, compounds compounds of Formula I demonstrate increased potency in causing the desired negative dromotropic effect to be used in therapeutic intervention. That is, these compounds have been found to most potently exert their therapeutic action upon conditions when this action is most required (i.e., tachycardia). This pharmacological profile offers the option of dosing patients with these compounds at levels that under normal conditions cause minimal or no action upon the heart, but under abnormal conditions of excessively rapid heart beats exert a therapeutic action.

Compounds of the present invention can be synthesized according to the methods described in U.S. Pat. Nos. 5,310,731 and 4,868,160. For example, compounds of Formula I may be obtained from 2',3'-O-isopropylideneinosine-5'-uronic acid by treatment with a suitable inorganic acid halide, such as thionyl chloride, to yield the intermediate, 6-chloro-9-[2,3-O-isopropylidene-β-D-ribofuranosyl-5-uronic acid chloride]-9H-purine. The intermediate, 6-chloro-9-[2,3-O-isopropylidene-β-D-ribofuranosyl-5-uronic acid chloride]-9H-purine, (or the corresponding bromide, if, for example thionyl bromide is used instead of thionyl chloride) need not be isolated in a pure state.

The acid chloride moiety of 6-chloro-9-[2,3-O-isopropylidene-β-D-ribofuranosyl-5-uronic acid chloride]-9H-purine (or the acid bromide of the corresponding bromo-analog) is significantly more readily displaced by nucleophilic reagents than the halide group in the 6 position of the purine moiety. Therefore, in accordance with the process of the present invention, 6-chloro-9-[2,3-O-isopropylidene-β-D-ribofuranosyl-5-uronic acid chloride]-9H purine is reacted with a first nucleophilic reagent having the formula $R_1$—$NH_2$ to yield an intermediate substituted carboxamide, wherein the halide is retained in the 6 position of the purine moiety.

The intermediate substituted carboxamide is subsequently reacted with a nucleophile having the formula $R_2$—$NH_2$ and the isopropylidene blocking group is removed with acid to yield the compounds of the invention, having free hydroxyl groups in the 2' and 3' positions of the ribofuranose moiety. Instead of the isopropylidene blocking group, other acid stable blocking groups can also be used to protect the 2'-OH and 3'-OH groups of the ribofuranose moiety during the step of treatment with the inorganic acid halide.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The pharmaceutically-acceptable esters of compounds of Formula I include organic acid esters of the hydroxyl groups at the 2' and 3' positions of the ribofuranose moiety. Ester groups are preferably of the type which are relatively readily hydrolyzed under physiological conditions. Useful esters include those having an acyl group selected from the group consisting of acetyl, propionyl, butyryl and benzoyl groups.

The present invention is also directed to the use of a compound of Formula I in the manufacture of a medicament for treating heart rhythm disturbances in a mammal that would benefit from the induction of negative dromotropic action, negative chronotropic action, or a combination thereof.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired. Preferred dosage routes are intravenous injection and oral administration.

There is need for rapid onset of action in conditions of heart rhythm disturbances since there can be a danger to heart tissue. Thus, intravenous injection is a first preferred administration route. Intravenous administration may consist of a single injection, a loading dose followed by continuous administration of a lower level maintenance dose, injections spaced over a period of time, continuous injection of a low level maintenance dose, or other types of administration that are suitable for the needs of the individual being treated.

A second preferred administration route is oral administration. Particular compounds of the invention have very high oral bioavailability. Oral administration is a particularly useful route for providing maintenance doses of compounds of the invention. Since the negative dromotropic effect of compounds of the invention increases as heart rate increases, patients can receive oral doses that exert a therapeutic effect when heart beat becomes excessively rapid.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 0.01 mg to 1 mg, preferably from 0.1 to 0.5 mg according to the particular application and the potency of the active ingredient. The compositions can, if desired, also contain other compatible therapeutic agents. Examples of useful therapeutic agents that can be co-administered with active compounds of the present invention include verapamil, quinidine, procainamide, diisopyramide, flecanide, ibutilide, dofetilide, amiodarone, sotalol, diltiazem, esmolol, propranolol, metoprolol, and digoxin. Further, DC cardioversion and surgical procedures are available for terminating atrial fibrillation and can be used in combination with the administration of compounds of the present invention.

In the therapeutic uses described above, the mammalian dosage range for a 70 kg subject is from about 0.00035 to about 1 mg/kg of body weight per day or preferably about 0.0007 to about 0.6 mg/kg of body weight per day. The dosages, however, may be varied depending upon the requirements of the patient, the severity of the condition being treated, and the compound being employed.

Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example. silica. talc, stearic acid or salts thereof, such as, magnesium stearate or calcium stearate, and/or polyethylene glycol. Dragee cores are provided with suitable coatings that, if desired, are resistant to gastric juices. For this purpose concentrated saccharide solutions can be used, which may optionally contain gum arabic, talc, polyvinyl pyrrolidone, polyethylene glycol, and/or titanium dioxide lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998. Formulations suitable for parenteral administration may be adjusted, if necessary, to a suitable pH to provide maximum stability and/or solubility for the active compound. The tonicity of such formulations may be adjusted with known tonicity adjusting agents. The concentration of active agents in parenteral formulations of the present invention is from about 0.1 to about 500 $\mu$g/mL, preferably about 1 to about 250 $\mu$g/mL and more preferably about 5 $\mu$g/mL to about 50 $\mu$g/mL. Parenteral formulations may be liquid, ready-to-use formulations or lyophilizates that can be reconstituted prior to administration.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

EXAMPLES

The following examples are illustrative, but not limiting, of the method and compositions of the present invention. Suitable modifications and adaptations of adaptations of the variety of conditions and parameters normally encountered and obvious to those skilled in the art are within the spirit and scope of the invention.

Concentration dose-effect curve data were fitted to a sigmoid curve using Graphpad PRIZM™ software to obtain the concentration or dose of test compound that produces 50% of the maximal obtainable response, in vitro $EC_{50}$ or in vivo $ED_{50}$ values, for activation of the adenosine $A_1$ receptor. Responses measured to each dose were the plateau negative inotropic response to cumulative additions of test compound in the isolated left atria and the peak bradycardia in response to bolus intravenous injections of test compound in conscious rats. Oral bioavailability was estimated from pharmacodynamic responses using the expression: (Response $AUC_{oral}$/Response $AUC_{iv}$)($Dose_{iv}$/$Dose_{oral}$), where Response AUC is the area under the curve for test compound-induced bradycardia over time.

Example 1

In vitro Activity

Male Sprague-Dawley rats weighing 200–350 grams were sacrificed and the hearts rapidly removed and placed in a warmed Krebs-Henseleit buffer solution. The left atria were dissected free from the hearts and suspended in 30 mL jacketed isolated organ baths filled with Krebs-Henseleit buffer, oxygenated with 95% $O_2$/5% $CO_2$ and maintained at 37° C. Tissues were connected to a force displacement transducer under a resting tension of 1 gram. Atria were stimulated electrically at 1 Hz, 1 msec duration and supramaximal voltage to produce regular contractions of tissue.

Adenosine $A_1$ agonists were added to the baths at increasing cumulative concentrations until a maximal decrease in the force of contraction was obtained. Because adenosine $A_1$ agonists have only a small direct negative inotropic action in rat atria, it was necessary to stimulate β-adrenergic receptors to produce positive inotropy in order to maximize the negative intropic response and thereby facilitate measurement. Under these conditions, adenosine $A_1$ agonists acting at $A_1$ receptors indirectly reduce the β-adrenergic mediated positive inotropy. Accordingly, the β-adrenergic agonist isoproterenol ($10^{-8}$ M) was added to the organ baths approximately 15 minutes before the addition of the adenosine $A_1$ agonist.

The results are expressed in the following table:

| Compound | $R_1$ | $R_2$ | $EC_{50}$ (nM) |
|---|---|---|---|
| A | cyclopentyl | ethyl | 15.5 |
| B | cyclopentyl | hydroxyethyl | 11.2 |
| C | cyclopentyl | cyclopropyl | 3.8 |
| D | cyclopentyl | methyl | 19.1 |
| E | cyclopentyl | isopropyl | 11.0 |
| F | cyclopentyl | t-butyl | 72.4 |
| G | cyclopentyl | propyl | 25.1 |
| H | norbornyl | hydroxyethyl | 3.8 |
| I | 3-pentyl | ethyl | 7.9 |
| J | 3-pentyl | hydroxyethyl | 21.8 |

These data demonstrate the high degree of in vitro potencies for this series of compounds at the adenosine $A_1$ receptor.

Example 2

In vivo Activity

Male Sprague-Dawley rats were anesthetized with sodium pentobarbital 50 mg/kg i.p., and indwelling catheters were surgically implanted in the carotid artery and jugular vein two days prior to each experiment. During all subsequent experiments, rats were conscious and unrestrained. The carotid artery cannula was attached to a pressure transducer and blood pressure was recorded continuously throughout each experiment using a Grass polygraph. Heart rate was derived from the blood pressure signal using a Grass tachygraph. The measured parameters were allowed from 30 to 90 minutes to stabilize before the administration of test compound.

Test compounds were administered either by oral gavage using a curved, bulbed oral dosing cannula, or by intravenous administration via the jugular vein indwelling catheter. Rats dosed orally were fasted overnight before dosing, with water available ad libitum. Because the heart rate responses following intravenous administration of test compound rapidly returned to baseline, more than one dose of test compound could be administered to each rat. However, the responses to oral administration of test compounds were of a prolonged duration and therefore only a single dose could be administered to each rat.

A comparison of the area under the bradycardia vs. time curve (AUC) following intravenous administration with the AUC following oral administration was used as a measure of oral bioavailability. The results are expressed in the following table:

| Compound | $R_1$ | $R_2$ | $ED_{50}$ (nmol/kg) | Oral Bioavailability |
|---|---|---|---|---|
| A | cyclopentyl | ethyl | 8.3 | 53% |
| B | cyclopentyl | hydroxyethyl | 7.4 | 8.4% |
| C | cyclopentyl | cyclopropyl | 9.3 | 38% |
| D | cyclopentyl | methyl | 3.9 | 20% |
| E | cyclopentyl | isopropyl | 3.4 | 28% |
| F | cyclopentyl | t-butyl | 363 | 34% |
| G | cyclopentyl | propyl | 32.3 | 14% |
| H | norbornyl | hydroxyethyl | 3.4 | 2.3% |
| I | 3-pentyl | ethyl | 7.9 | 20% |
| J | 3-pentyl | hydroxyethyl | 8.3 | 9.9% |

Substantial oral bioavailability is a critically important quality in a compound in order to permit ease of chronic administration. It is apparent from these data that the 5'-hydroxyethyl substituent interferes with oral bioavailability and that the 5'-alkyl-substituted derivatives (said alkyl containing from one to three carbons) have good oral activity.

Example 3

Differentiation of Negative Dromotropic Activity from Coronary Vasodilation

Rat isolated hearts were prepared according to the method of Langendorff in which the coronary vasculature was perfused in a retrograde fashion at constant pressure via the aorta. Coronary blood flow was determined by measuring the volume of fluid leaving the heart. Heart rate was maintained at 360 beats per minute by electrical pacing of the right atrium. Atrioventricular (AV) conduction was determined as the time from the atrial stimulus to the beginning of ventricular depolarization (S-V interval).

Compound A produced concentration-dependent slowing of AV conduction, with a maximal increase in S-V interval at a mean concentration of 6.8 nM and AV conduction blockade at a mean concentration of 8.3 nM. At these concentrations, Compound A had no effect on coronary blood flow. This demonstrates that Compound A is a potent adenosine $A_1$ receptor agonist that induces a maximal negative dromotropic action at doses that have no effect on coronary vasodilation.

Example 4

Differentiation of Negative Chronotropic Activity from Hypotensive Activity

Male Sprague-Dawley rats were anesthetized with sodium pentobarbital 50 mg/kg i.p., and indwelling catheters were surgically implanted in the carotid artery and jugular vein two days prior to each experiment. During all subsequent experiments, rats were conscious and unrestrained. The carotid artery cannula was attached to a pressure transducer and blood pressure was recorded continuously throughout each experiment using a Grass polygraph. Heart rate was derived from the blood pressure signal using a Grass tachygraph. The measured parameters were allowed from 30 to 90 minutes to stabilize before the administration of test compound.

Compound A was administered by intravenous administration via the jugular vein indwelling catheter or by oral gavage using a curved, bulbed oral dosing cannula. Food and water were available ad libitum.

The $ED_{50}$ value found for induction of bradycardia was 0.1 μg/kg/min intravenously for 120 minutes, which caused a mean 34% decrease in heart rate while mean blood pressure remained unchanged. An intravenous dose range of 0.05 μg/kg/min to 0.1 μg/kg/min was demonstrated to cause no change in blood pressure. Similarly, an oral dose range of 30 μg/kg to 100 μg/kg caused no change in blood pressure, with the 100 μg/kg dose causing a mean 40% decrease in heart rate. This demonstrates that highly significant negative chronotropic effects are apparent for the exemplified compound at doses having no effect on blood pressure.

Example 5

Demonstration of Negative Dromotropic and Negative Chronotropic Activity in the Spontaneously Beating Heart Guinea pig isolated hearts were prepared according to the method of Langendorff in which the coronary vasculature was perfused in a retrograde fashion at constant pressure via the aorta. Compound A was administered to the spontaneously beating hearts by infusion into the perfusion line supplying buffer to the coronary vasculature. The concentration of Compound A was adjusted by changes in the infusion rate and/or changes in the concentration of infusion solutions. The concentration of Compound A present in the perfusate was calculated by dividing the rate of Compound A infused by the coronary flow rate. Spontaneously beating heart rate and AV interval were recorded.

Figure 1:
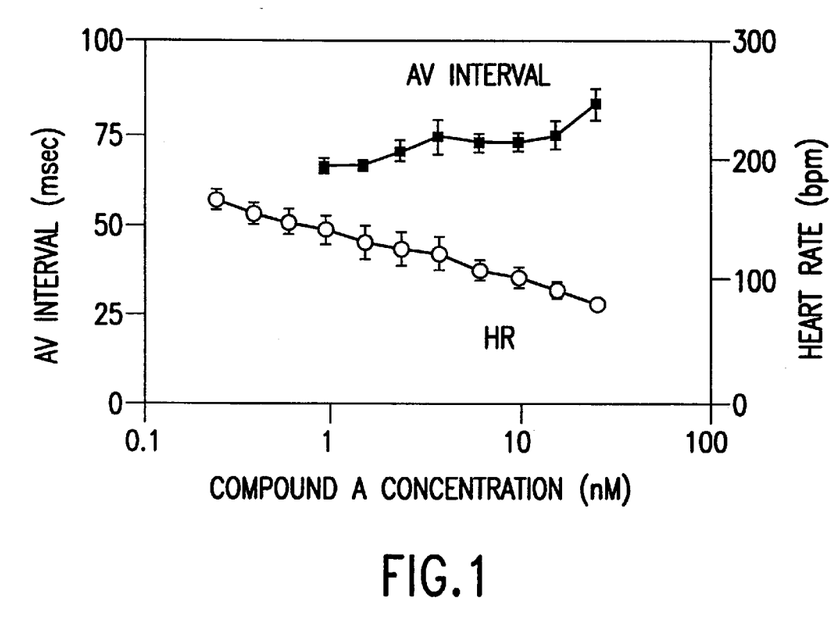
FIG. 1 depicts negative chronotropic and negative dromotropic actions of ethyl N⁶-cyclopentyladenosine-5'-uronamide (Compound A) in the guinea pig isolated spontaneously beating heart; HR=heart rate, bpm=beats per minute, msec=milliseconds. Compound A produced concentration-dependent slowing of AV conduction, with the maximal increase in AV interval representing a 34% increase over basal values. Compound A also produced a concentration-dependent decrease in heart rate, with an $EC_{50}$ value of 3.2 nM and a maximal decrease in heart rate of 58%.

The results of the experiment are shown in FIG. 1. Compound A produced concentration dependent slowing of AV conduction, with the maximal increase in AV interval representing a 34% increase over basal values. Compound A also produced a concentration-dependent decrease in heart rate, with an $EC_{50}$ value of 3.2 nM and a maximal decrease in heart rate of 58%.

Example 6

Demonstration of the Effect of Heart Rate on Negative Dromotropic Activity

Guinea pig isolated hearts were prepared according to the methods described in Example 5. In the first portion of the experiment designed to determine the effect of heart rate on the negative dromotropic activity of Compound A, hearts were allowed to beat spontaneously or electrically paced either at 200 beats per minute (approximately 20% above the spontaneous rate) or at 300–360 beats per minute (approximately 80% above the spontaneous rate). Atrioventricular (AV) conduction interval (AV interval) was determined as the time from the atrial stimulus to the beginning of ventricular depolarization. The AV interval measurements were performed at each pacing rate with increased concentrations of Compound A as described in Example 5. Upon electrical pacing at 200 beats per minute, Compound A at a mean concentration of 3.9 nM produced a mean maximal 58% increase in AV interval, and heart block at a mean minimal concentration of 5.1 nM. Upon electrical pacing at 300–360 beats per minute, Compound A at a mean concentration of 1.45 nM produced a mean maximal 20% increase in AV interval, and heart block at a mean minimal concentration of 2.1 nM. The results are summarized in the table below, with data from spontaneously beating hearts included for comparative purposes:

| Heart Rate (bpm) | Mean Concentration of Compound A Required to Produce Maximal AV Interval (nM) | Mean Minimal Concentration of Compound A Required to Produce Heart Block (nM) |
| --- | --- | --- |
| Spontaneous (appro. 170) | 11.7 | 13 |
| 200 | 3.9 | 5.1 |
| 300–360 | 1.45 | 2.1 |

These data demonstrate that the negative dromotropic effect produced by the exemplified compound is rate-dependent, with increased potency for Compound A demonstrated as the pacing rate was increased.

Example 7

Figure 2:
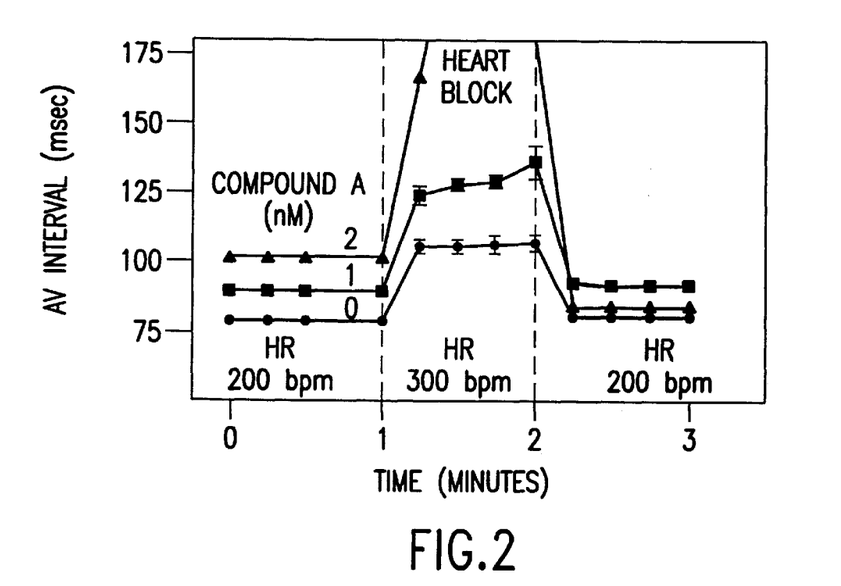
FIG. 2 depicts negative dromotropic actions of Compound A in the guinea pig isolated heart model of paroxysmal supraventricular tachycardia (PSVT); HR=heart rate, bpm=beats per minute, msec=milliseconds. Compound A, at a mean concentration of 2 nM that had little effect on AV interval at 200 bpm pacing, induced AV block within 30 seconds during the 300 bpm pacing episode. When pacing was returned to 200 bpm, the AV interval also returned to near normal values. The effects of Compound A in this experimental model of PSVT are, therefore, rate dependent such that Compound A produces greater increase in AV conduction interval at higher pacing rates.

Demonstration of Negative Dromotropic Activity in Experimental Model of Paroxsymal Supraventricular Tachycardia Using the experimental conditions described in Example 6, individual hearts were paced at 200 bpm for one minute followed abruptly by one minute of pacing at 300 bpm, after which the pacing rate was returned to 200 bpm. The 300 bpm pacing cycle was intended to simulate an episode of supraventricular tachycardia. This pacing sequence was conducted in the presence of vehicle and in the presence of increasing concentrations of Compound A. The results are expressed in FIG. 2. Compound A, at a mean concentration of 2 nM that had little effect on AV interval at 200 bpm induced AV block within 30 seconds during the 300 bpm episode. When the pacing rate was returned to 200 bpm, the AV interval also returned to near normal values.

Example 8

Figure 3:
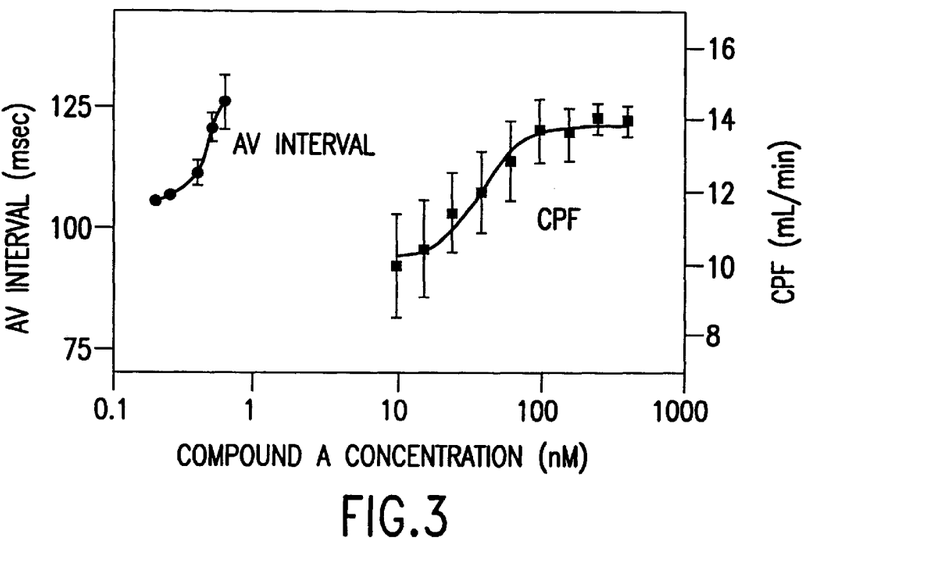
FIG. 3 depicts negative dromotropic and coronary vasodilator actions of Compound A in the guinea pig isolated electrically-paced heart; CPF=coronary perfusate flow, mL=milliliters. Under pacing conditions of 300–360 beats per minute, Compound A at a mean concentration of 0.76 nM produced a mean maximal 23% increase in AV interval, and heart block at a mean concentration of 1.09 nM. Under these same pacing conditions, Compound A produced concentration-dependent increases in coronary perfusate flow from a mean flow rate of 8.5 mL/min to a mean flow rate of 14.2 mL/min. The mean concentration of Compound A producing a 50% maximal increase in coronary perfusate flow ($EC_{50}$) was 32 nM. Compound A was, therefore, greater than 40-fold more potent at slowing AV conduction than at increasing coronary perfusate flow.

Differentiation of Negative Chronotropic Activity from Coronary Vasodilation in Paced Hearts In order to determine the differential potencies of Compound A for negative chronotropic activity versus coronary vasodilation in paced hearts, a different set of experiments was conducted in which individual hearts were used to collect measurements for each action. Experimental conditions as described in Example 6 were used, with guinea pig isolated hearts being paced at 300–360 beats per minute. AV conduction interval was determined as described in Example 6. Coronary perfusate flow data was determined by measuring the volume of fluid leaving the heart. AV conduction interval data and coronary perfusate flow data were collected in the presence of increasing concentrations of Compound A. The results are shown in FIG. 3, with dose-related increases for both AV conduction interval and coronary perfusate flow. The differential for these effects is readily apparent. The mean concentration of Compound A that produced a maximal increase in AV conduction time was 0.76 nM. The concentration of Compound A that produced a half maximal effect in coronary perfusate flow ($EC_{50}$) was 32 nM. Compound A is greater than 40 fold more potent at slowing AV conduction time that it was for increasing coronary perfusate flow.

Having now fully described this invention, it will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. A method for the treatment of heart rhythm disturbances in a human in need thereof that would benefit from the induction of negative dromotropic and/or negative chronotropic actions, comprising the administration to said human an effective amount of a compound of the Formula:

or a pharmaceutically acceptable salt or ester thereof, wherein $R_1$ is $C_{3-7}$ secondary alkyl, $C_{3-8}$ cycloalkyl, or $C_7$ bicycloalkyl; and $R_2$ is $C_{1-4}$ alkyl, $C_{1-4}$ hydroxyalkyl or $C_{3-5}$ cycloalkyl;

wherein said effective amount produces the desired therapeutic effect, and wherein the effective amount is administered orally or intravenously in the amount of 0.001–100 µg/kg.

2. The method of claim 1, wherein:

$R_1$ is 3-pentyl, cyclopentyl, or norbornyl; and $R_2$ is methyl, ethyl, isopropyl or cyclopropyl.

3. The method of claim 1, wherein said compound is administered in a parenteral dosage form.

4. The method of claim 3, wherein said compound is intravenously injected.

5. The method of claim 1, wherein said compound is administered in an oral dosage form.

6. The method of claim 1, wherein $R_2$ is ethyl.

7. The method of claim 1, wherein $R_2$ is cyclopropyl.

8. The method of claim 1, wherein $R_1$ is 3-pentyl.

9. The method of claim 1, wherein $R_1$ is cyclopentyl.

10. The method of claim 9, wherein $R_2$ is ethyl.

11. The method of claim 9, wherein $R_2$ is cyclopropyl.

12. The method of claim 4, wherein said compound is selected from the group consisting of:

$N^6$-cyclopentyl-5'-(N-ethyl)carboxamidoadenosine, $N^6$-cyclopentyl-5'-(N-cyclopropyl)carboxamidoadenosine, $N^6$-(3-pentyl)-5'-(N-ethyl)carboxamidoadenosine, $N^6$-cyclopentyl-5'-(N-methyl)carboxamidoadenosine, and $N^6$-cyclopentyl-5'-(N-t-butyl)carboxamidoadenosine, as well as pharmaceutically acceptable salts and esters thereof.

13. The method of claim 4, wherein said compound is $N^6$-(3-pentyl)-5'-(N-ethyl)carboxamidoadenosine.

14. The method of claim 3, wherein said compound is $N^6$-cyclopentyl-5'-(N-ethyl)carboxamidoadenosine.

15. The method of claim 3, wherein said compound is $N^6$-cyclopentyl-5'-(N-cyclopropyl)carboxamidoadenosine.

16. The method of claim 5, wherein said compound is $N^6$-cyclopentyl-5'-(N-ethyl)carboxamidoadenosine.

17. The method of claim 5, wherein said compound is $N^6$-cyclopentyl-5'-(N-cyclopropyl)carboxamidoadenosine.

18. The method of claim 1, wherein said heart rhythm disturbance is a supraventricular tachyarrhythmia.

19. The method of claim 1, wherein said heart rhythm disturbance is paroxsymal supraventricular tachycardia.

20. The method of claim 1, wherein said heart rhythm disturbance is atrial fibrillation.

21. The method of claim 3, wherein said compound is administered by intravenous infusion in an amount of from 0.001 µg/kg to 100 µg/kg.

22. The method of claim 21, wherein said compound is administered by intravenous infusion in an amount of from about 0.005 µg/kg to about 1 µg/kg.

23. The method of claim 22, wherein said compound is administered by intravenous infusion in an amount of from about 0.01 µg/kg to about 0.5 µg/kg.

24. The method of any one of claims 3 or 21–23, wherein said compound is administered within a period of from about 2 to about 60 minutes.

25. The method of claim 24, wherein said compound is administered within a period of from about 10 to about 30 minutes.

26. The method of claim 4, wherein said compound is administered intravenously in an amount of from about 0.1 µg/kg/min to about 10 µg/kg/min.

27. The method of claim 5, wherein said compound is administered in an amount of from about 0.001 µg/kg to about 10 µg/kg.

28. The method of claim 27, wherein said compound is administered in an amount of from about 0.01 µg/kg to about 8 µg/kg.

29. The method of claim 5, wherein said compound is administered at a dose of from about 1 to about 50 µg/kg.

30. The method of claim 29, wherein said dose is administered up to four times a day.

* * * * *